(12) United States Patent
Eyrard et al.

(10) Patent No.: US 10,918,600 B2
(45) Date of Patent: *Feb. 16, 2021

(54) DRY ACID CONCENTRATE IN GRANULATE FORM

(71) Applicant: Fresenius Medical Care Deutschland GmbH, Bad Homburg (DE)

(72) Inventors: Thierry Eyrard, Lyons (FR); Philippe Laffay, Sainte Foy les Lyon (FR); Benoit Luaire, Sourcieux les Mines (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 73 days.

This patent is subject to a terminal disclaimer.

(21) Appl. No.: 16/174,311

(22) Filed: Oct. 30, 2018

(65) Prior Publication Data

US 2019/0070116 A1  Mar. 7, 2019

Related U.S. Application Data

(63) Continuation of application No. 15/116,947, filed as application No. PCT/EP2015/000251 on Feb. 6, 2015, now Pat. No. 10,245,231.

(30) Foreign Application Priority Data

Feb. 7, 2014  (EP) .................................... 14000455

(51) Int. Cl.
| | | |
|---|---|---|
| *A61K 9/16* | (2006.01) | |
| *A61M 1/16* | (2006.01) | |
| *A61K 31/194* | (2006.01) | |
| *A61K 31/7004* | (2006.01) | |
| *A61K 33/14* | (2006.01) | |

(52) U.S. Cl.
CPC .............. *A61K 9/16* (2013.01); *A61K 9/1682* (2013.01); *A61K 31/194* (2013.01); *A61K 31/7004* (2013.01); *A61K 33/14* (2013.01); *A61M 1/1656* (2013.01); *A61M 1/1666* (2014.02); *A61M 1/1668* (2014.02)

(58) Field of Classification Search
CPC .... A61K 9/16; A61K 31/194; A61K 31/7004; A61K 33/14; A61K 9/1682; A61M 1/1656; A61M 1/1666; A61M 1/1668
See application file for complete search history.

(56) References Cited

U.S. PATENT DOCUMENTS

| | | |
|---|---|---|
| 2010/0120702 A1 | 5/2010 | Sugiyama et al. |
| 2013/0004593 A1 | 1/2013 | Kloeffel et al. |
| 2013/0183389 A1 | 7/2013 | Carlsson et al. |
| 2017/0007541 A1 | 1/2017 | Eyrard et al. |

FOREIGN PATENT DOCUMENTS

| | | |
|---|---|---|
| EP | 0417478 A1 | 3/1991 |
| EP | 1192961 A2 | 4/2002 |
| JP | S64-025725 A | 1/1989 |
| JP | H10-330270 A | 12/1998 |
| JP | 2006218319 A | 8/2006 |
| JP | 2007131563 A | 5/2007 |
| WO | 2011073274 A1 | 6/2011 |

OTHER PUBLICATIONS

Office Action received in corresponding Japanese Patent Application No. 2016-568111 dated Dec. 10, 2018 (English translation attached) (13 pages).

International Search Report from corresponding PCT/EP2015/000251 dated Mar. 30, 2015.

Nichols et al., "A Review of the Terms Agglomerate and Aggregate with a Recommendation for Nomenclature Used in Powder and Particle Characterization," Journal of Pharmaceutical Sciences, 2002, vol. 91, No. 10, pp. 2103-2109.

*Primary Examiner* — Genevieve S Alley

(74) *Attorney, Agent, or Firm* — Kilyk & Bowersox, P.L.L.C.

(57) ABSTRACT

The present invention relates to a novel dry acid concentrate (DAC) for a dialysis liquid and to a dialysis liquid, which is made from said concentrate, and which may be used for purifying blood. The invention further relates to a method of making the dry acid concentrate as well as the dialysis liquid. It also relates to a container (10) comprising said acid concentrate, and which is—in certain embodiments—specially adapted to a dialysis unit.

20 Claims, 5 Drawing Sheets

DRY ACID CONCENTRATE IN GRANULATE FORM

Figure 1:
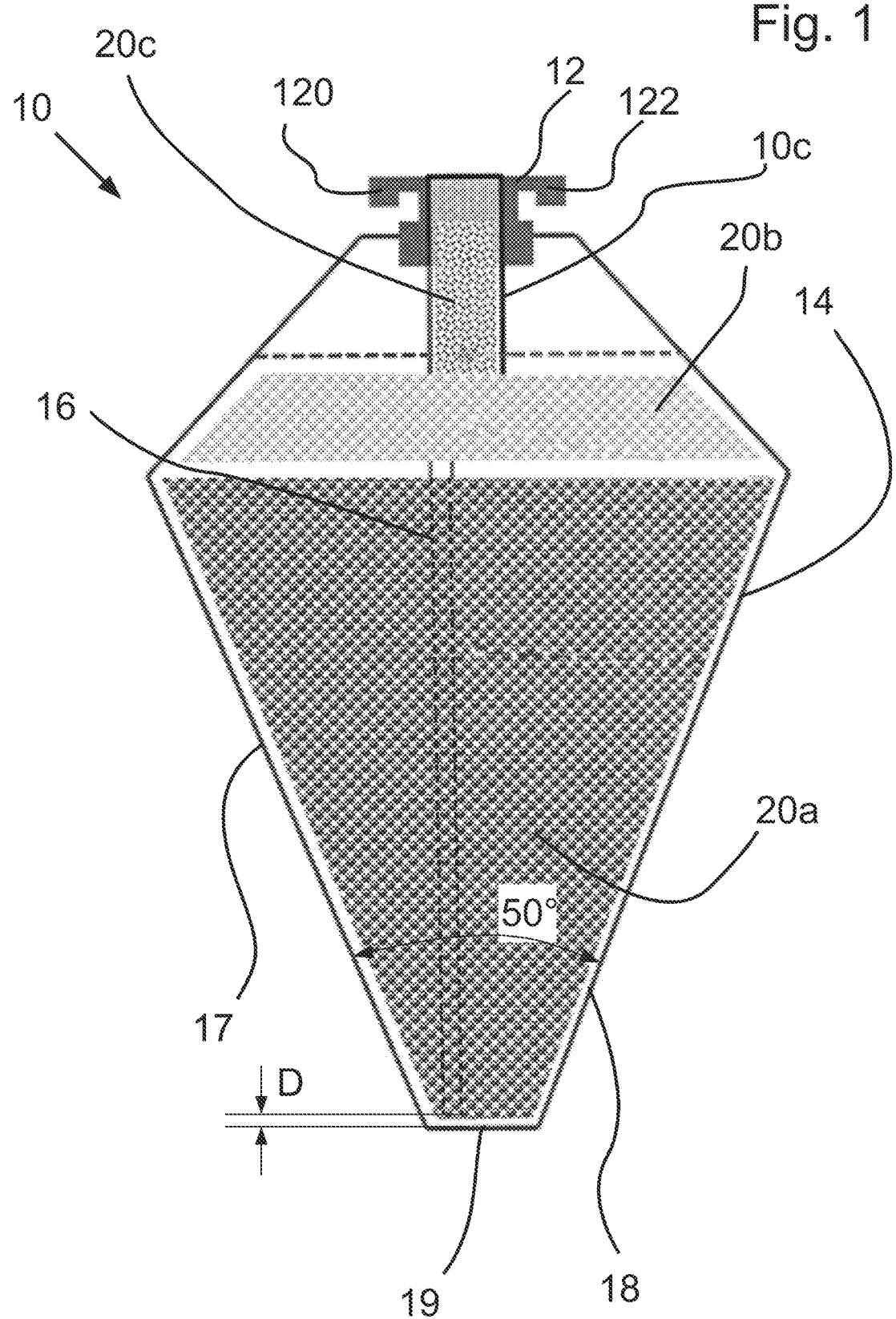

This application is a continuation of U.S. patent application Ser. No. 15/116,947, filed Aug. 5, 2016, which is a National Stage Application of PCT/EP2015/000251, filed Feb. 6, 2015, which claims priority to EP 14 000 455.7, filed Feb. 7, 2014.

FIELD OF THE INVENTION

Introduction

The present invention relates to a novel dry concentrate suitable to form a liquid acid concentrate or a part of a liquid acid concentrate for a dialysis liquid and to a dialysis liquid, which is made from said concentrate, and which may be used for purifying blood. The invention further relates to a method of making said dry concentrate as well as the dialysis liquid. It also relates to a container (10) comprising said acid concentrate, and which is—in certain embodiments—specially adapted to a dialysis unit.

BACKGROUND OF THE INVENTION

A so-called acid concentrate is usually used in the manufacture of a dialysis solution in addition to a base concentrate comprising bicarbonate. The acid concentrate comprises a solution of a plurality of components which are usually present in different amounts and/or concentrations. Typical components are NaCl as the main component and the other electrolytes such as KCl, $CaCl_2$ and $MgCl_2$ in smaller amounts. The dry concentrate may comprise NaCl and the other three electrolytes in a ratio of about 9 to 1. The acid concentrate may also contain glucose and a pH-adjusting agent, e.g. an organic acid, such a citric acid. The specifications for the concentrations of the electrolytes are very tight, which has the consequence that all the components of the acid concentrate have to be completely dissolved before the use of the acid concentrate in the proportioning or metering unit for manufacturing the dialysis solution. This cannot take place in flow as with the base concentrate. It is rather the case that special mixing apparatus such as stirrers have to be used here to ensure this complete dissolving in an acceptable time period.

Against this background, the named acid concentrate is usually supplied as a liquid concentrate in a canister from which the liquid concentrate is removed by means of the dialysis- or a preparation unit and is used for manufacturing the finished dialysis solution. A disadvantage in the use of such canisters is the comparatively complex handling as well as the relatively high weight, which brings about disadvantages with respect to the transportation and storage costs as well as with regard to the handling of the same for the clinic personal.

In clinics in which a larger number of treatment stations are present, ring lines are sometimes also used which are connected to a central supply unit. The acid liquid concentrate is manufactured or made available with the aid of special mixing apparatus in this central supply unit and is then fed into the ring line. It is led off from the ring line at the dialysis unit or at the treatment stations and is then available to the dialysis unit for preparing the ready-to-use dialysis solution. In this procedure no problems with regard to the composition and the mixing occur. One disadvantage of this procedure is that the disinfection and cleaning of such a system is laborious, expensive and pollutive and moreover that this type of concentrate supply is only economical for larger treatment centers due to the relatively high costs.

One solution for the above-referenced problem is disclosed in WO 2013/004362 of the present applicant. It relates to a container containing at least one dry concentrate, wherein the dry concentrate is of such a nature that, when it is dissolved in a liquid, e.g. in water, it forms at least one acidic liquid concentrate or part of an acidic liquid concentrate that is suitable for producing at least one dialysis solution. The container is adapted such that it can be connected to the dialysis unit via one or more connecting means. A further solution is disclosed in WO 2011/073274, again of the present applicant. It relates to a method of dissolving/mixing of a concentrate in/with a fluid in a multi-chamber bag, to a method for the production of a ready-to-use medical fluid, in particular a dialysis fluid, in a multi-chamber bag and to the multi-chamber bag itself.

Solid compositions for the preparation of dialysis solutions in granular form are also known in the art. In this regard, reference is made to US 2007/023139, which relates to a solid pharmaceutical preparation for dialysis, which comprises two solid pharmaceutical preparations (A) and (B), wherein pharmaceutical preparation (A) contains one or more electrolytes selected from the group consisting of sodium chloride, calcium chloride, magnesium chloride, and potassium chloride and an organic acid other than acetic acid and/or a salt of the organic acid, and wherein the solid pharmaceutical preparation (B) contains sodium bicarbonate. This preparation is prepared by a spray-drying granulation process.

EP 1 120 110 relates to a composition for the preparation of a dialytic solution which contains all the components or ingredients known per se and used for the preparation of the acid solution and the basic solution to be used in dialysis, wherein these ingredients form part of at least one granulate in which the ingredients are present in predetermined and constant ratios.

Further preparations to be used for dialysis in the form of a granulate are disclosed in U.S. Pat. No. 6,210,803, EP 0 417 478 and EP 2 151 247, which compositions respectively contain granulates made of granules which respectively contain all electrolytes required for a ready-to-use solution for hemodialysis.

The introduction of water to the granular preparations according to the prior art leads to the formation of hardly soluble particles, which led to problems with the accuracy of the exact ratio of constituents needed in the dry concentrate or at least significantly enhance the time of dissolution.

In view of the above situation, it is one object of the present invention to provide a dry concentrate suitable to form a liquid acid concentrate or a part of a liquid acid concentrate having improved dissolution characteristics in order to even further ensure that the resulting dialysis liquid contains the necessary constituents in the physiologically necessary amounts and proportions to each other.

It is another object to provide a dry concentrate suitable to form a liquid acid concentrate or a part of a liquid acid concentrate comprising all necessary constituents in the necessary relative amounts without elaborate weighing procedures, which would be the case when all constituents are to be weighed individually.

It is another object to provide a dry concentrate suitable to form a liquid acid concentrate or a part of a liquid acid concentrate that can be provided ready-to-use within a dialysis unit for one treatment of one patient.

It is a further object to provide a liquid acid concentrate in a manner to avoid the transport of heavy canisters and/or the provision of complex ring line systems, stated differently, it was an object to provide a dry concentrate suitable to form a liquid acid concentrate or a part of a liquid acid concentrate in an appropriate form for the instantaneous preparation of dialysis solutions, in line, ready for immediate use.

SUMMARY OF THE INVENTION

In view of the above objects, the invention provides a dry concentrate suitable to form a liquid acid concentrate or a part of a liquid acid concentrate usable in dialysis comprising
a first component comprising a first granulate comprising a plurality of first granules comprising sodium chloride and glucose, and
a second component comprising a second granulate comprising a plurality of second granules, wherein said granules comprise at least one further physiologically acceptable electrolyte, which is different from sodium chloride,
or a second component in the form of a powder, wherein said powder comprises at least one further physiologically acceptable electrolyte which is different from sodium chloride, and wherein said powder comprises a plurality of fine particles, wherein each particle comprises or consists of one of said at least one further physiologically acceptable electrolyte,
or a mixture of said granulate and said powder.

In one embodiment of the dry concentrate the first and the second component comprise or consist of said first and second granulate.

In one embodiment of the dry concentrate the granules of the first component exhibit a higher average equivalent diameter than the granules of the second component.

In one embodiment of the dry concentrate the first granulate comprises at least 50 wt-%, e.g. at least 75 wt-% or. at least 90 wt-% of granules, respectively based on the total weight of the first granulate in the dry concentrate, which have an equivalent diameter of above 0.5 to below 12.5 mm.

In one embodiment of the dry concentrate the second granulate comprises at least 50 wt-%, e.g. at least 75 wt-% or at least 90 wt-% of granules, respectively based on the total weight of the first granulate in the dry concentrate, which have an equivalent diameter of above 1 to below 5 mm.

In one embodiment of the dry concentrate said second component comprises a cation selected from the cations of magnesium, calcium, potassium, or mixtures of two or more thereof; and comprises an anion selected from chloride, acetate, lactate, or mixtures of two or more thereof, e.g. wherein the second component comprises $MgCl_2$, $CaCl_2$ and KCl.

The dry concentrate may further comprising citric acid as a third component.

In another embodiment, the invention relates to a dry concentrate, wherein the granulates of the first component or the first and the second component are obtainable via a manufacturing process comprising the following step(s):
dry compressing said NaCl and glucose to obtain first compacts, or dry compressing said NaCl and glucose, and the at least one further physiologically acceptable electrolyte to obtain first and second compacts, wherein said dry compressing of said first and said dry compressing of said second compacts are conducted separately from each other;
reducing the size of said first compacts to form a first granulate comprising a plurality of first granules,
or reducing the size of said first and second compacts to form a first and second granulate comprising a plurality of first and second granules.

In one embodiment the separate dry compressing of the first and second compacts comprises the step of passing the NaCl and glucose or the NaCl and glucose and the at least one further physiologically acceptable electrolyte under pressure between two rolls with parallel axes, which are driven in mutually counter-rotating rotation sense.

In one embodiment the reduction of size is achieved by grinding, milling, crushing, or a combination of two or more thereof.

In one embodiment said steps of dry compressing and reduction of size are carried out continuously.

In another embodiment, the invention relates to a process for the preparation of the dry concentrate comprising the following step(s):
dry compressing said NaCl and glucose to obtain first compacts, or dry compressing said NaCl and glucose, and the at least one further physiologically acceptable electrolyte to obtain first and second compacts, wherein said dry compressing of said first and said dry compressing of said second compacts are conducted separately from each other;
reducing the size of said first compacts to form a first granulate comprising a plurality of first granules,
or reducing the size of said first and second compacts to form a first and second granulate comprising a plurality of first and second granules.

In one embodiment the dry compressing comprises the step of passing the NaCl and glucose or the NaCl and glucose and the at least one further physiologically acceptable electrolyte under pressure between two rolls with parallel axes, which are driven in mutually counter-rotating rotation sense.

In one embodiment the reduction of size is achieved by grinding, milling, crushing, or a combination of two or more thereof.

In one embodiment said steps of dry compressing and reduction of size are carried out continuously.

In one embodiment said manufacturing process comprises the sieving of said granulates obtained by reducing the size of said compacts through at least two sieves, e.g. through exactly two sieves. The manufacturing process may include a step of re-introducing the granules having a size above a desired maximum equivalent diameter or below a desired minimum equivalent diameter into said compressing step. In one embodiment it includes a step of re-introducing all granules into said compressing step.

In another embodiment, the invention relates to a container (10) comprising at least the dry concentrate according to the invention.

In one embodiment, said container (10) is designed such that it has at least one connection means (12) by means of which the container (10) can be coupled to a dialysis unit or to a preparation unit for an acid liquid concentrate.

In one embodiment the container (10) may comprise the first and second and optionally third component in separate compartments. It may also comprise the first and the second component in one compartment and, if present, the third component in a second compartment. It may also comprise the first, the second and the third component, if present, in one compartment. In one embodiment, these compartments or this compartment contains only said first and/or second and/or third component, i.e. besides those components no additional constituents are present.

In one embodiment, the container (10) has at least one introduction means (16) by which at least one liquid, e.g.

water, or at least one liquid, e.g. water, and a gas, e.g. air, can be introduced into the container (10) for the purpose of dissolving the dry concentrate (20), with the introduction means (16) being formed as a hose or at least comprising a hose.

In one embodiment, the introduction means (16) is dimensioned such that it projects up to and into the dry concentrate (20).

In one embodiment said at least one introduction means (16) projects, starting from an upper container wall, from above into the interior of the container (10) and down to and into the bottommost point of the inner space of the container (10) and ends close to the bottommost point of the container (10), e.g. 5 (±3) mm above said bottommost point of the container (10), wherein said bottommost point of the container (10) is located along the wall opposite to the introduction means (16). Said introduction means may be in the form of a hose.

In one embodiment, the container (10) has wall regions (17, 18) which face toward one another in at least one region and between which a trough-shaped region (19) or a recess is formed, with the dry concentrate (20) being at least also present in the trough-shaped region (19) or in the recess in the operating position of the container (10), e.g. wherein the inclined wall regions (17,18) form an angle between 30° and 70°, or 40° to 60°, in particular 50° between each other.

In one embodiment, the container (10) has the following characteristics:
it comprises at least one connection means (12) by means of which the container (10) can be coupled to a dialysis- or to a preparation unit for an acid liquid concentrate;
it comprises at least one introduction means (16) in the form of a hose, which projects, starting from an upper container wall hosting the introduction means (16), from above into the interior of the container (10) and down to and into the bottommost point of the inner space of the container (10) and ends 5 (±3) mm above said bottommost point of the container (10), and wherein said bottommost point of the container (10) is located along the wall opposite to the introduction means (16); and
the container (10) has wall regions (17, 18) which face toward one another in at least one region and between which a trough-shaped region (19) or a recess is formed, with the dry concentrate (20) being at least also present in the trough-shaped region (19) or in the recess in the operating position of the container (10), wherein the inclined wall regions (17,18) form an angle between 30° and 70°, in particular 50° between each other.

In one embodiment, the container (10) is made as a stand-up container.

In one embodiment, the container (10) has at least two films or precisely two films, which form the container walls, with one of the films having a folded section in the empty state of the container (10), which forms a container wall in the filled state of the container (10).

In one embodiment, the container (10) as such, i.e. without the dry concentrate, is adapted to contain a dry concentration of the invention and has the following characteristics:
it comprises at least one connection means (12) by means of which the container (10) can be coupled to a dialysis- or to a preparation unit for an acid liquid concentrate;
it comprises at least one introduction means (16) in the form of a hose, which projects, starting from an upper container wall hosting the introduction means (16), from above into the interior of the container (10) and down to and into the bottommost point of the inner space of the container (10) and ends 5 (±3) mm above said bottommost point of the container (10), and wherein said bottommost point of the container (10) is located along the wall opposite to the introduction means (16); and
the container (10) has wall regions (17, 18) which face toward one another in at least one region and between which a trough-shaped region (19) or a recess is formed such that a dry concentrate (20) can be also present in the trough-shaped region (19) or in the recess in the operating position of the container (10), wherein the inclined wall regions (17,18) form an angle between 30° and 70°, e.g. 50° between each other.

In one embodiment, the container (10) contains the dry concentrate in the appropriate amount for one dialysis treatment of one patient.

In another embodiment, the invention relates to a dialysis or preparation unit, wherein the preparation unit serves to prepare a liquid concentrate to be used for the preparation of a dialysis solution, comprising at least one dry concentrate of the invention. The dialysis or preparation unit may also comprise one or more of the containers (10) as described within the invention, wherein the container (10) is connected to the dialysis or preparation unit.

In another embodiment, the invention relates to a method of preparing a liquid acid concentrate which in turn serves the preparation of a dialysis solution, at least comprising step (i) of mixing the dry concentrate with water.

In one embodiment, said step (i) is carried out in the presence of a gas, e.g. air.

In one embodiment, said mixing is carried out under at least one of the following conditions, in one embodiment under a combination of conditions 2), 5) and 6):

1) the mixing is carried within the container (10) of the invention;
2) the mixing is carried within a container (10) with the following characteristics:
   it comprises at least one connection means (12) by means of which the container (10) can be coupled to a dialysis- or to a preparation unit for an acid liquid concentrate;
   it comprises at least one introduction means (16) in the form of a hose, which projects, starting from an upper container wall hosting the introduction means (16), from above into the interior of the container (10) and down to and into the bottommost point of the inner space of the container (10) and ends 5 (±3) mm above said bottommost point of the container (10), and wherein said bottommost point of the container (10) is located along the wall opposite to the introduction means (16); and
   the container (10) has wall regions (17, 18), which face toward one another in at least one region and between which a trough-shaped region (19) or a recess is formed such that a dry concentrate (20) can be also present in the trough-shaped region (19) or in the recess in the operating position of the container (10), wherein the inclined wall regions (17,18) form an angle between 30° and 70°, e.g. 50° between each other;
3) the mixing is carried out in the presence of water and air, wherein water is added to the container (10) with a velocity of 600 to 800 ml/min;
4) the mixing is carried out in the presence of water and air, wherein air is added to the container (10) with a velocity of 1 to 3 l/min;
5) the mixing is carried out in the presence of water and air, wherein water is added to the container (10) with a velocity of 600 to 800 ml/min and air is added to the container (10) with a velocity of 1 to 3 l/min;

6) the mixing is carried out at a temperature of from 50° C. to 65° C., e.g. 55° C. to 60° C.

In one embodiment, the method of preparing a liquid acid concentrate is carried out such that a complete dissolution of the concentrate is achieved within less than 10 minutes, e.g. in 5 to less than 10 minutes, or 7 to 9 minutes.

In one embodiment, said method is carried out within the dialysis or preparation unit at a point in time, where no dialysis takes place.

DETAILED DESCRIPTION OF THE INVENTION

In a first aspect the invention is directed to a dry concentrate suitable to form an acid liquid concentrate or a part of an acid liquid concentrate usable in dialysis.

The term "dry concentrate" as used herein means that in the concentrate, if at all, only minor amounts of water are present. The water amount may be less than 10 wt.-%, e.g. less than 5 wt.-%, based on the total amount of concentrate.

Said dry concentrate is one that is "suitable to form an acid liquid concentrate or a part of an acid liquid concentrate". This term does not provide a significant limitation for the dry concentrate of the present invention and rather sets out that said dry concentrate can and in fact should be mixed with water with the aim to provide a (part of) an acid liquid concentrate, which in turn is useable for dialysis purposes, in particular as one constituent of the dialysis solution to be applied to the patient. It, however, provides a limitation in that the dry concentrate is substantially free of any base components, which are suitably used in dialysis, such as sodium bicarbonate. In one embodiment, the first and the second component are respectively also substantially free from any acid components that are suitably used in dialysis. In another embodiment, the first and/or the second component are substantially free of any base components, which are suitably used in dialysis, but additionally comprise an acid component, such as citric acid. In a further embodiment, said additional acid component is contained in said second component. In the context of the present application, the term "substantially free" means that the amounts of base and/or acid component in said dry concentrate, e.g within the first and/or second granulate, are such that without the addition of additional base and/or acid component no dialysis solution can be prepared. In one embodiment, the dry concentrate is free of any base components. In another embodiment, the first and second component are free of any acid components. In another embodiment, the first and second component are free from any base component, but one of the two components comprises the acid component.

The dry concentrate comprises a first component comprising a first granulate, which comprises a plurality of first granules comprising sodium chloride and glucose.

It further comprises a second component comprising a second granulate, which comprises a plurality of second granules, which respectively comprise at least one, e.g. at least two, e.g. three further physiologically acceptable electrolytes, which are different from sodium chloride. In one embodiment the second component comprises a powder comprising a plurality of fine particles, wherein each of said fine particles comprises or consists of one of said further physiologically acceptable electrolyte, which is different from sodium chloride. The second component may also be a mixture of said second granulate and said powder.

The term "component" as used herein means a part of the concentrate.

The term "granulate" as used herein relates to a plurality of granules which form the granulate. The term "granule" is used herein in its broadest meaning and relates to a small particle that is gathered into an aggregate, wherein the individual particle size of the particle can still be determined. The granulate may contain a plurality of granules which are heterogeneous or homogeneous in size. The granules of the first and the second component, respectively comprise at least two constituents, namely NaCl and glucose (first granules) and at least one, e.g. at least two, e.g. three further physiologically acceptable electrolytes being different from NaCl (second granules). For preparing the granulate any manufacturing process known in the art may be used. The first and the second granulate are different from each other. This is immediately apparent from claim 1 itself, which stipulates the difference between the electrolytes within the granulates. However, the first and the second granulate may be different from each other in further aspects, such as size, shape and method of manufacture.

The term "powder which comprises at least one further physiologically acceptable electrolyte which is different from sodium chloride", as used herein, and denoted hereinunder also as "powder", relates to a dry, bulk solid composed of a large number of very fine particles that may flow freely when shaken or tilted. Each individual fine particle comprises or consists of only one of said further physiologically acceptable electrolytes.

The first granulate comprises a plurality of first granules comprising NaCl and glucose. In one embodiment the first granulate consists of said plurality of first granules. In a further embodiment the first granules comprise 50 to 100 wt-%, e.g. 75 wt-% or more or 90 wt-% or more of NaCl and glucose. In a still further embodiment the first granulate consists of a plurality of first granules, which comprise 50 to 100 wt-%, e.g. 75 wt-% or more or 90 wt-% or more of NaCl and glucose.

In one embodiment the first granules comprises no other active constituent suitably used for a dialysis solution/dry concentrate apart from NaCl and glucose. In this embodiment, other constituents, such as binders, may be present in said first granules. Thus, it is also within the ambit of the present application to provide a granulate suitable to be used as a component within a dry concentrate as defined herein, which comprises a plurality of granules, which comprise NaCl and glucose as the only active constituents of a dialysis solution. In one embodiment these first granules consist of NaCl and glucose.

The second granulate comprises a plurality of second granules, which in turn comprises at least one, e.g. at least two, e.g. three further physiologically acceptable electrolytes, which are different from sodium chloride. In one embodiment the second granulate consists of said plurality of second granules. In a further embodiment the second granules consist of 50 to 100 wt-%, e.g. 75 wt-% or more or 90 wt-% or more of said at least one, e.g. at least two, e.g. three further physiologically acceptable electrolytes. In a still further embodiment the second granulate consists of a plurality of second granules, which comprise 50 to 100 wt-%, e.g. 75 wt-% or more or 90 wt-% or more of said at least one, e.g. at least two, e.g. three further physiologically acceptable electrolyte.

In a further embodiment, the second component comprises a powder comprising at least one further physiologically acceptable electrolyte, which is different from sodium chloride. Said powder comprises a plurality of fine particles, wherein each of said fine particles comprises or consists of one of said further physiologically acceptable electrolytes. In a further embodiment the fine particles consist of 50 to 100 wt-%, e.g. 75 wt-% or more or 90 wt-% or more of said one further physiologically acceptable electrolyte. In a still further embodiment the second components consists of said powder, which comprise 50 to 100 wt-%, e.g. 75 wt-% or more or 90 wt-% or more of said at least one further physiologically acceptable electrolyte.

In a further embodiment the dry concentrate comprises the first and the second component in the form of said first and second granulates.

In one embodiment the granules within the first and second granulate are predominantly irregularly-shaped, i.e. not round particles. In this embodiment, the granules of the first component exhibit a higher average equivalent diameter than the granules of the second component.

The term "average equivalent diameter" or "equivalent diameter" refers to (the average of) the diameter of an irregularly-shaped object, here, granule or fine particle, that corresponds to the diameter of a spherical particle as determined by sieving through a sieve with round holes. Granules having an "equivalent diameter in the range of above 0.5 to below 12.5 mm" are granules that are able to pass through a sieve with holes having a diameter of 12.5 mm in any orientation, but are unable to pass a sieve having holes with a diameter of 0.5 mm in some orientation. The term "equivalent diameter" is used herein for irregular and regular, i.e. round or spherical particles, respectively. Needless to say that for spherical granules and fine particles the equivalent diameter corresponds to their diameter.

The same relation also applies in cases where the granules are predominantly round and the dimensions of the granules may be determined via their diameter; i.e. the average diameter of the granules of the first granulate is higher compared to those of the second granulate.

This difference in average particle size between the first and the second component has the advantage of a still further improved dissolution profile in water such that all constituents within the dry concentrate may be dissolved concurrently. The exact size and size difference necessary to optimize the dissolution behavior of the first and second component may be determined by the person skilled in the art based on routine experimentation.

In one embodiment the first granulate comprises at least 50-wt-%, e.g. at least 75-wt-% or e.g. at least 90-wt-% of granules having an equivalent diameter in the range of above 0.5 to below 12.5 mm, e.g. above 0.8 to below 8.0 mm. In a further embodiment up to 100 wt-% of the first granules within the first granulate fulfill this equivalent diameter range.

In another embodiment the second granulate comprises at least 50%, e.g. at least 75% or e.g. at least 90% of granules having an equivalent diameter in the range of above 1 to below 5 mm, e.g. above 1.2 to below 4.8 mm. In a further embodiment up to 100 wt-% of the second granules within the second granulate fulfill this diameter range.

In one embodiment the first and/or the second granulate may comprise granules that are not within the specification, and which are smaller in equivalent diameter than the specification requires. In one embodiment at least 80 wt-% of the total of the granules that are not within the specification exhibit an equivalent diameter that is smaller than the lower limit of the specification.

In a still further embodiment the first and the second granulate both fulfill the above mentioned conditions as to their size in terms of the equivalent diameter.

The first component comprises NaCl and glucose. The glucose may be present in the first component in the form of its monohydrate or in anhydrous form. The term also encompasses D-glucose (also denoted as dextrose) and L-glucose as well as racemates of D- and L-glucose. It may further comprise additives such as pH adjusting agents.

The second component comprises at least one of the further electrolytes necessarily to be used in an acid dialysis solution.

The term "electrolyte" as used herein, comprises all electrolytes, which do not cause intolerances or adverse effects in and at the patients during dialysis.

In one embodiment, the physiologically acceptable electrolyte has cations selected from the cations of magnesium, calcium, potassium, or from mixtures of two or more thereof. Within this embodiment, the anions may be selected from chloride, acetate, lactate, or two or more of these anions.

In one embodiment, as physiologically acceptable electrolyte, salts are used selected from: calcium chloride, magnesium chloride, calcium lactate, magnesium lactate, calcium acetate, magnesium acetate, or from combinations of two or more thereof.

In one embodiment, the first component in the form of a granulate comprises NaCl and glucose, and the second component comprises $CaCl_2$, $MgCl_2$ and KCl and is also in the form of a granulate.

In another embodiment the concentrate comprises a third component which may be citric acid or another suitable acid, e.g. citric acid.

According to a second aspect the invention relates to a process of preparing the dry concentrate. This process encompasses the provision of the first component in the form of a first granulate and the provision of the second component in the form of a second granulate or a powder.

Thus, the process comprises a granulating step. Therefore, the process of preparation of the first and second component in the form of a granulate comprises the weighing out/provision of the constituents individually and forming a first and a second granulate. The first and the second granulate may be obtained by separately granulating/preparing the same and forming the dry concentration by combining, e.g. mixing, the two separately prepared granulates.

Within the ambit of the present invention any kind of granulation including dry and wet granulation methods known in the art may be used, such as fluidized-bed granulation, agitating granulation, pan coating and wet granulation. With regard to further details as to the methods of granulation available to prepare the granulates of the dry concentrate particular reference is made to U.S. Pat. No. 6,210,803 by the applicant, as well as EP 2 151 247 and EP 0 602 014.

In one embodiment, the granulation process as disclosed in EP 0 287 978 is used. Compared to the fluidized bed granulation well known in the art, this granulation method is significantly more economical, e.g. in terms of energy consumption. The granulation process according to EP 0 287 978 is a continuous process, wherein the components are continuously provided into the granulation means.

Thus, the present application relates to process for the preparation of the dry concentrate as described herein comprising the following step(s):

dry compressing said NaCl and glucose, or the at least one further physiologically acceptable electrolyte, or said NaCl and glucose, and the at least one further physiologically acceptable electrolyte to obtain first and second compacts, wherein said dry compressing of said first and said dry compressing of said second compacts are conducted separately from each other;

reducing the size of said first compacts to form a first granulate comprising a plurality of first granules, or reducing the size of said first and second compacts to form a first and second granulate comprising a plurality of first and second granules, or reducing the size of the first compacts to form a first granulate comprising a plurality of first granules and reducing the size of the second compacts to form a powder.

In one embodiment the dry compressing comprises the step of passing said NaCl and glucose or said NaCl and glucose and the at least one further physiologically acceptable electrolyte under pressure between two rolls with parallel axes, which are driven in mutually counter-rotating rotation sense.

The reduction of size may be achieved by any method known in the art, such as grinding, milling, crushing, or a combination of two or more thereof.

Furthermore, said steps of dry compressing and reduction of size are carried out continuously.

In a further embodiment said preparation process comprises the sieving through at least two sieves, in one embodiment through exactly two sieves, of said granulates obtained by reducing the size of said compacts. In a further embodiment the granules having a size above the desired maximum size or below the desired minimum size are re-introduced into said compressing step. In a further embodiment all granules are re-introduced into said compressing step. This sieving and re-introduction into the compressing step may be carried out several times and leads to a more homogeneous size distribution of the granules within the granulates. It also minimizes the amount of in some embodiments unwanted very small particles (dust) and, generally, of granules having a size outside the specification In addition, the invention also relates to a dry concentrate obtainable by the method of preparation defined hereinbefore, namely a dry concentrate comprising a first component in the form of a first granulate as defined hereinabove and a second component in the form of a second granulate or a powder, as respectively as defined hereinabove, wherein the first and/or the second granulate are obtained via a granulation procedure.

In one embodiment, the invention relates to a dry concentrate as defined hereinabove, wherein the granulates of the first or the second component or the first and the second component are obtainable via a manufacturing process comprising the following step(s):

dry compressing said NaCl and glucose, or the at least one further physiologically acceptable electrolyte, or said NaCl and glucose, and the at least one further physiologically acceptable electrolyte to obtain first and second compacts, wherein said dry compressing of said first and said dry compressing of said second compacts are conducted separately from each other;

reducing the size of said first compacts to form a first granulate comprising a plurality of first granules, or reducing the size of said first and second compacts to form a first and second granulate comprising a plurality of first and second granules, or reducing the size of the first compacts to form a first granulate comprising a plurality of first granules and reducing the size of the second compacts to form a powder;

e.g. wherein the dry compressing comprises the step of passing the NaCl and Glucose or the NaCl and glucose and the at least one further physiologically acceptable electrolyte under pressure between two rolls with parallel axes, which are driven in mutually counter-rotating rotation sense; and/or e.g. wherein the reducing of size is achieved by grinding, milling, crushing, or a combination of two or more thereof; and/or e.g. wherein said steps of dry compressing and reduction of size are carried out continuously.

The resulting dry concentrate may be provided in a one-piece form or in a multi-part form, for example in a two-part form or in a three-part form. This means that the two or three components of the dry concentrate may be provided as a mixture of all components, e.g. within a container (10) comprising only one compartment, or may be provided in separate compartments of a container (10) or in separate containers (10), respectively.

In one embodiment, the first and the second component are provided within one compartment of a container (10) or in one container (10), while the third component, i.e. the citric acid, is provided in a separate compartment of the same container (10) or is contained within a separate container (10).

In a third aspect the invention relates to a liquid acid concentrate being prepared from said dry concentrate. In order to arrive at a liquid concentrate, the dry concentrate of the subject invention has to be admixed with water, e.g. ultrapure water. This is achieved by means known in the art, e.g. in a dialysis or preparation unit prior to starting the dialysis.

In a fourth aspect the invention relates to a container (10) comprising the dry concentrate of the invention.

The term "container" as used herein encompasses terms such as "packaging" or "bag" or "cartridge". In one embodiment, the term "container" means also a container, which, e.g., may be removed from a dialysis unit or a device, which is connected to a dialysis unit, and may be reinserted into said unit. In a further embodiment, the term "container" means also that said container is accessible for water and/or a physiologically acceptable electrolyte solution, e.g. a sodium chloride solution, in order to dissolve the components, which are present in the container (10), and/or to release protons from them.

In said embodiments, the container (10) has typically such a volume that, in addition to the dry concentrate, liquid, e.g. water, can be received or is received in a volume of 1 to 15 liters or 2 to 14 liters, or 3 to 13 liters, or 4 to 6 liters, to manufacture the acid liquid concentrate by dissolving the dry concentrate and/or that the container (10) has a total volume in the range from 1 to 15 liters or 2 to 14 liters, or 3 to 13 liters, or 4 to 6 liters.

The dry concentrate can be present in the container (10) in an amount of 0.5 kg to 6 kg, e.g. in an amount of 0.75 kg to 5.5 kg, further e.g. in an amount of 1.0 kg to 5.0 kg, and particularly e.g. in an amount of 1.3 to 4.2 kg. Such containers (10) allow a problem-free handling, are easy to transport and to store and are suitable for carrying out one or more hemodialysis treatments.

It is possible that the dry concentrate is composed such that the acid liquid concentrate obtained on its dissolution in a volume of 2 to 15 liters, or of 4 to 15 liters has a pH<7.0.

It is in particular conceivable that the dry concentrate is contained in the container (10) in a quantity such that on its dissolution in a volume of 4 to 15, e.g. 4 to 6 liters of liquid, e.g. water, a liquid concentrate results, with the dry concentrate e.g. being completely dissolved.

Generally, the dissolution for manufacturing the finished dialysis solution is performed in situ, and the amount and proportions of the constituents of the components as well as the container size and amount of water is adjusted such that the constituents are e.g. present in the following concentration ranges (in mmol/l) with respect to the volume of the finished dialysis solution:

| | | | | | |
|---|---|---|---|---|---|
| NaCl: | 110-170 | mmol/l, | e.g. | 130-150 | mmol/l |
| KCl: | 0.7-4.3 | mmol/l, | e.g. | 1.0-4.0 | mmol/l |
| CaCl$_2$: | 0.7-2.0 | mmol/l, | e.g. | 1.0-1.7 | mmol/l |
| MgCl$_2$: | 0.3-1.2 | mmol/l, | e.g. | 0.5-1.0 | mmol/l |
| Glucose: | 0.8-2.2 | g/l, | e.g. | 1.0-2.0 | g/l |
| Citric acid: | 0.1-20 | mmol/l, | e.g. | 1.0-15.0 | mmol/l, |

All values relate to the finished dialysis solution. It is, for example, conceivable that 34 liters of a mixture of water and the base concentrate are mixed with 1 liter of the acid liquid concentrate to obtain 35 liters of ready-to-use dialysis solution. This mixing ratio naturally applies not only to the above-named example, but can be assumed as a suitable mixing ratio in general.

The below table shows typical embodiments of the concentration (in mmol/l) of the relevant constituents stemming from the dry concentrate of the subject invention in the (ready-to-use) dialysis solution as well as the liquid acid concentrate in various concentration grades.

| | Concentration of the constituents in the dialysis solution stemming from the acid concentrate | Concentration within the liquid acid concentrate 30-fold | Concentration within the liquid acid concentrate 45-fold | Concentration within the liquid acid concentrate 37-fold |
|---|---|---|---|---|
| Na+ | 103 | 3090 | 4635 | 3811 |
| Cl— | 110 | 3300 | 4950 | 4070 |
| Ca2+ | 1.5 | 45 | 67.5 | 55.5 |
| Mg2+ | 0.5 | 15 | 22.5 | 18.5 |
| K+ | 2 | 60 | 90 | 74 |
| K+ | 3 | 90 | 135 | 111 |
| K+ | 4 | 120 | 180 | 148 |
| Citric acid | 1 | 30 | 45 | 37 |

For preparing the dialysis solution, typically 35 mmol/l sodium bicarbonate are added, which results in a sodium concentration within the dialysis solution of 138 mmol/l. The mixing ratios within the device for preparing the (ready-to-use) dialysis solution are 1 part acid concentrate, 1.6 to 3.3 parts base concentrate, typically a saturated sodium bicarbonate solution, and about 30 to about 40 parts water.

In one embodiment, the amount and ratio of components within said dry concentrate are used such that together with the appropriate amount of water a liquid acid concentrate results that is suitable to be used for one treatment of one patient. Within this embodiment, the container (10) comprising the appropriate amounts of a first and second and optionally third component is filled with a total amount of water of 4157 ml. The resulting liquid concentrate is diluted within the dialysis or preparation unit in a ratio of 1:37. Water is added to the container (10) with a velocity of 600 to 800 ml/min, e.g. 700 ml/min together with air at a velocity of 1 to 3 l/min, e.g. 2 l/min. In one embodiment said dissolution is carried out at a temperature in the range of 50 to 65° C. Further details regarding the provision of such a liquid concentrate for one treatment of one patient may also be deduced from the example hereinafter.

Particularly suitable containers (10) are disclosed in WO 2013/004362 and WO 2013/020989, whose contents are incorporated herein by reference. Besides the container material and shape, WO 2013/020989 also discloses suitable connection means to connect the container (10) to the dialysis or preparation unit as well as introduction means for water and/or air necessary to reliably and quickly provide a liquid acid concentrate.

As to the shape of the container (10), in particular to the section opposite to the connection means (12) with the wall region (17, 18) facing towards each other and forming a trough shaped region (19) reference is made to FIG. 1 of WO 2013/020989 and the corresponding description.

In one embodiment, the container (10) is fixedly connectable to the dialysis- or to a preparation unit. As to the corrector means reference in made again to WO2013/004362 and the prior art cited therein.

In another embodiment, the container (10) may also include the base concentrate, however, in any case in a separate compartment.

In one embodiment not only water, but also air, is introduced through the connection means of the container (10) and through the coupling means of the dialysis- or of the preparation unit or through a corresponding fluid connection of these means/unit, and further e.g. through a hose or the like, into the container (10) for the purpose of dissolving the dry concentrate. Respective connector means are known in the art and e.g. disclosed in EP 1 344 550 B1.

Deviating from the teaching of EP 1 344 550 B1, provision is e.g. made within the framework of the present invention that a connector part serves for the supply of air and of the solvent, in particular water, as well as also for the removal of the liquid concentrate. The other connector part serves, within the framework of the present invention, only for the removal of gas or air from the container (10).

Provision can furthermore be made that the container (10) has at least one coding by means of which the container (10) and/or the dry concentrate and/or the liquid acid concentrate can be identified.

As to further details regarding the coding, the venting, outlet and introduction means, again reference is made to WO 2013/04263.

Figure 2:
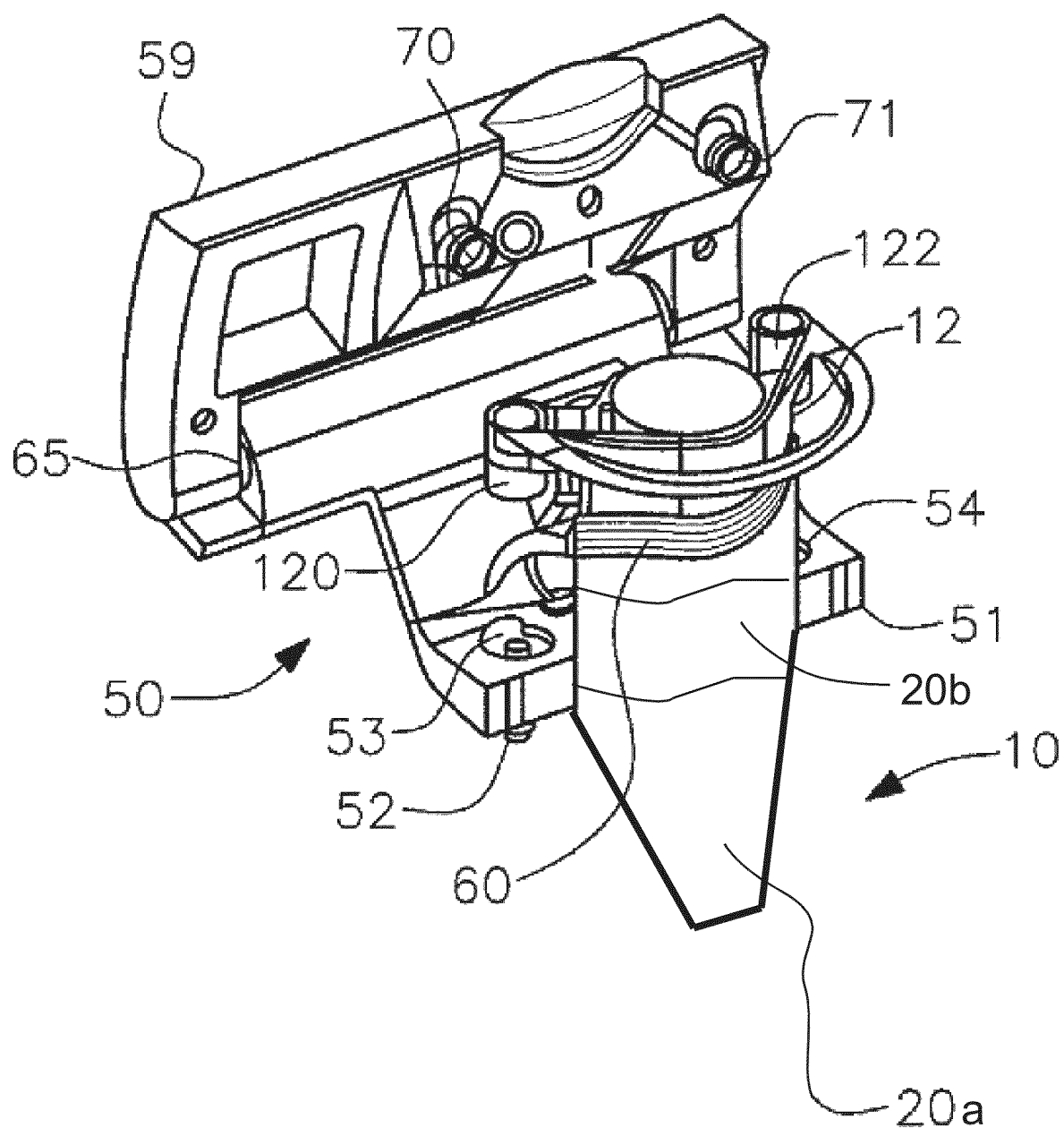
Figure 3:
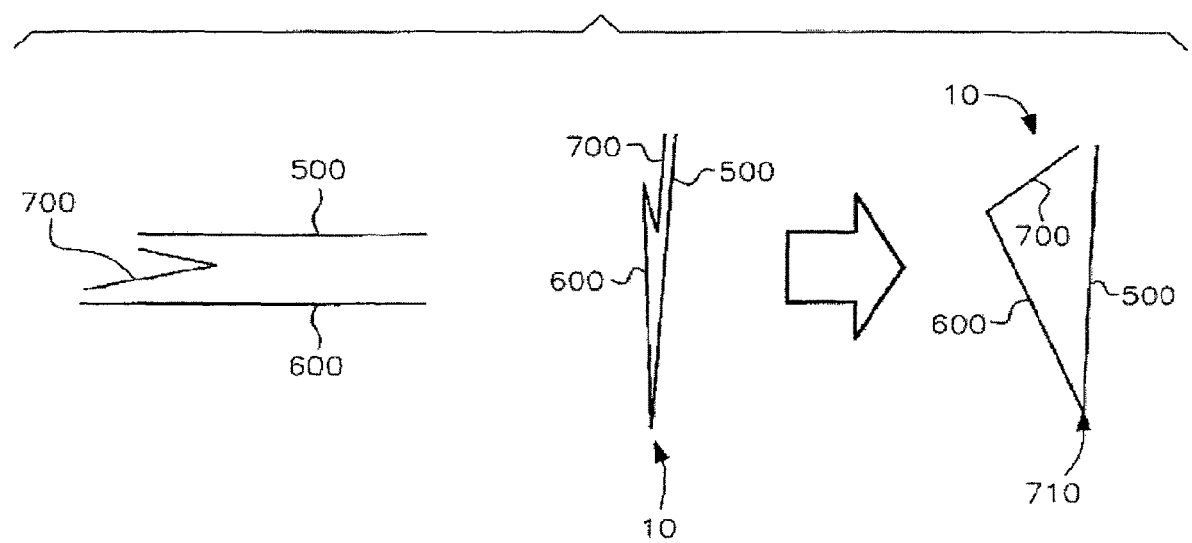
Figure 4:
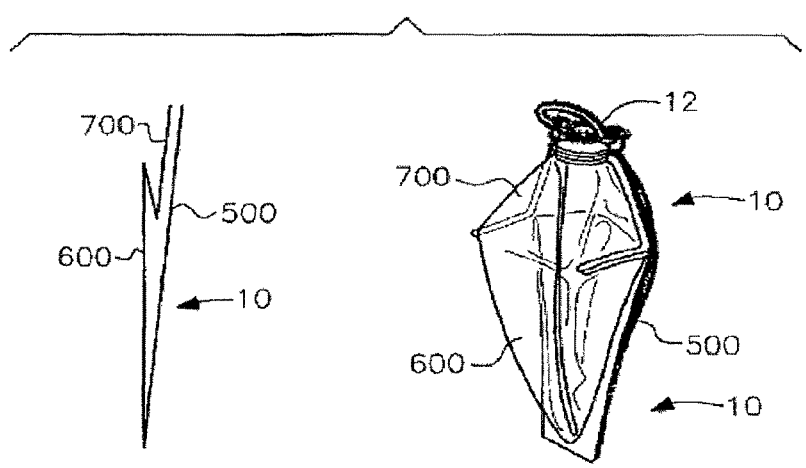
Figure 5:
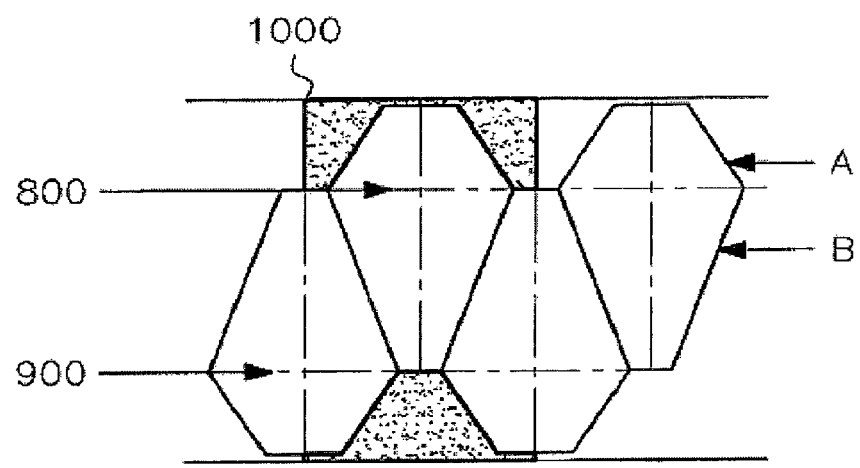
Figure 6:
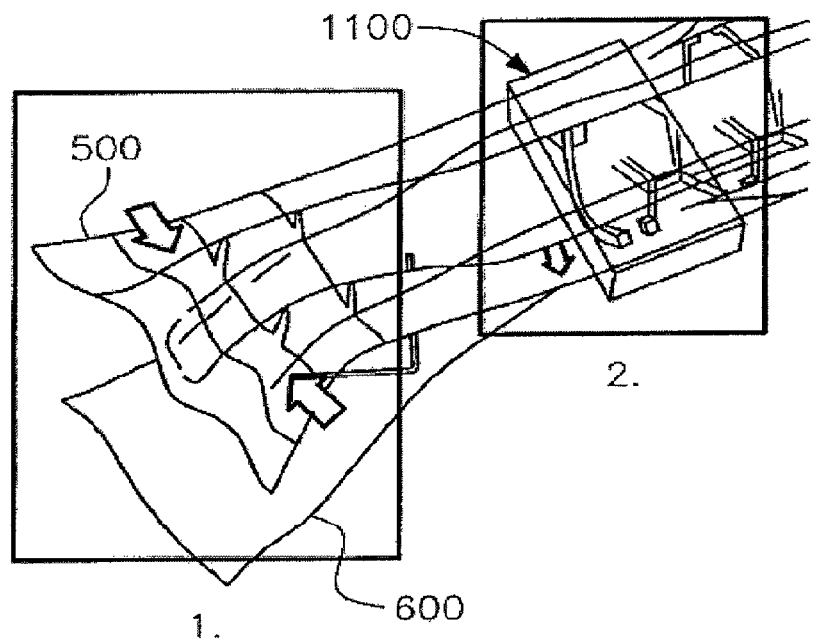
Figure 7:
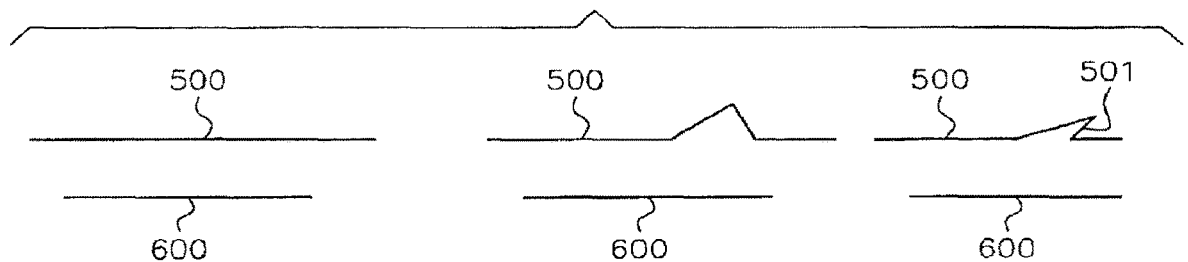

One particular embodiment of the container (10) according to the fourth aspect of the invention is now described with regards to the figures. There are shown:

FIG. 1: a schematic view of a container (10) in accordance with the invention which is partly filled with dry concentrate;

FIG. 2: a perspective view of a receptacle in accordance with the invention as well as a coupling region of a dialysis- or of a preparation unit before the coupling of the receptacle;

FIG. 3: a schematic view of an embodiment of the container (10) in accordance with the invention during manufacture and well as during the opening procedure;

FIG. 4: a longitudinal sectional view through a container (10) in accordance with the invention as well as a perspective view of the container (10) in accordance with the invention;

FIG. 5: a plan view of the film web for manufacturing the container (10);

FIGS. 6, 7: schematic representations of the manufacturing process.

FIG. 1 shows a schematic view of the container 10 in the operating position. Two wall sections 17, 18 are located which are both designed as sloping with respect to the horizontal and are made falling respectively from the outside to the inside and form a trough-shaped region 19 between them, which in turn forms the bottommost point or region in which the dry concentrate is located in the inner container space.

Thus, the container 10 has wall regions 17, 18 between which a trough-shaped or depression-shaped region 19 forms, with the dry concentrate 20 being at least also present in the trough-shaped region 19 in the operating position of the container 10. It can be ensured in this manner that the dry concentrate "slides on" into the named trough-shaped region 19 and is thus present at a central position in which favorable conditions apply for the dissolving of the dry concentrate. In the preferred embodiment, the value of the angle between the wall regions 17 and 18 is 50° as indicated in FIG. 1. Also containers 10 having inclined wall regions 17, 18 with an angle of 30° to 90°, e.g. 40° to 60°, such as 50° there between realize the advantageous effect of the depression-shaped region 19.

Provision is thus e.g. made that the container 10 has at least one, or a plurality of funnel-like constrictions, and indeed in the lower end region of the container 10. It is thus ensured that the non-dissolved dry concentrate is located directly at the point of delivery of the fluid or liquid and air during the total dissolving procedure and is to continuously swirled. The time for the complete dissolving of the concentrate is in particular reduced to a favorable time period by this measure.

The introduction means 16, i.e. the hose, the line or the like, e.g. extends up to and into the trough-shaped region 19 or up to and into the funnel-like constriction. The distance D between the lower end of the pipe 16 and the bottommost point of the container 10 of a preferred embodiment is about 5 mm, e.g. 5 mm+/−3 mm. Also containers 10 having distances D of 2 mm to 8 mm between the lower end of the pipe 16 and the bottommost point of the container 10 allow an effective operation of the container 10.

As can further be seen from FIG. 1, the container 10 is not completely filled with one type of concentrate 20. The dry concentrate comprises the following substances: electrolytes, glucose and citric acid or another suitable acid in solid or liquid form. In a preferred embodiment, about 90% of the container is filled with NaCl/dextrose granules 20a which is optimized for dissolution. Upon this concentrate, minor granules 20b are filled, which is optimized for excellent homogeneity.

The container 10 is connected my means of a connection element 12 which will be described later. In one embodiment, at the top of the container 10 a tank 10c is arranged with an opening mechanism which can be a rigid piston with cutting shape or also a piercable membrane when using a soft tank or the like. Within the tank 10c a citric acid 20c is stored, e.g. in powder form. Within FIG. 1 this mechanism is already open. In another embodiment, the constituents 20a to 20c are stored in said container 10 without any opening mechanism, i.e. the constituents 20a to 20c are present in one compartment.

The bag 10 has a special connection element 12 in its region shown at the top in the Figure with which the bag can be suspended at a dialysis unit or at a filling station which is also called a preparation unit within the framework of the present invention. The connection element 12 can be made such that it can be connected, e.g. in a fluid-tight and/or gas-tight manner, to a special coupler of the dialysis- or of a preparation unit. This connection can be established, for example, by a simple plugging on or by a rotary movement or by a screw connection.

After establishing this connection, liquid and/or gas can be introduced into the container 10 by means of the line 16. As soon as the dry concentrate is completely dissolved, the acid liquid concentrate can likewise be drawn out of the container 10 by means of the line 16. The line 16 projects, starting from an upper container wall, from above into the interior of the container 10 and down to and into the lowest point of the inner space of the container 10 or into the dry concentrate present there.

As can further be seen from FIG. 1 the bag has an inflow 16 which is formed in the manner of a hose 16 and whose open end lies at the above-named lowest point 19 of the container 10. The inflow or the hose 16 is provided in its end region projecting into the container 10 with a filter or the like as protection to prevent the penetration of the dry concentrate into the interior of the hose 16.

The filling with water, the introduction of air and the drawing off of the liquid concentrate takes place through the line 16. The produced liquid concentrate can be mixed with a volume of water, e.g. RO water, to be able to produce the finished dialysis solution. The base liquid concentrate, which can likewise be obtained by dissolving a dry concentrate in a container 10 coupled to the dialysis- or to a preparation unit, can be metered in before or after the addition of the acid liquid concentrate.

To allow the escape of air from the container 10 on its filling with water and/or air, a venting element is provided (not shown in FIG. 1) which can be connected to the dialysis- or the preparation unit. This venting element can be formed by a filter, e.g. being arranged in the bag wall or in the region of the connection means 12. This filter should be made such that it allows air and liquid to pass through, but no powder or granulate so that it cannot unintentionally move out of the container 10.

If a plurality of dialysis treatments are carried out after one another with the same container 10, it is possible to carry out an intermediate disinfection between the treatments. It is conceivable to do the filling before the purging, with no contamination risk being present since it is the primary circuit.

FIG. 2 shows an exemplary embodiment of the container 10 in accordance with the invention with the connection means 12 which serves the coupling to the coupling means of a preparation- or a dialysis unit.

The arrangement, which can be seen from FIG. 2 represents in a preferred embodiment an arrangement in accordance with the invention for the coupling of a container 10 to the dialysis- or to a preparation unit which is generally marked by the reference numeral 50.

Air and water can be introduced through the port 52 of the dialysis- or the preparation unit by the connection means 12 to the container 10 and through the hose 16 into the lower region of the container 10. For this purpose, a connection of the port 52 to the connection 120 at the container side takes place.

The container 10 or its connection means 12 is connected via a further coupler or connector 122 to the dialysis- or the preparation unit. The correspondingly associated line is marked by the reference numeral 51.

Air is removed from the container 10 through the port or the line 51 during the dissolving process or during the filling process of the container 10 with water and air.

Different from the teaching known from EP 1 344 550 B1, the line 52 or the line 16 in accordance with the present invention does not only serve the supply of water and air, but also the leading off of the dissolved concentrate. It is drawn off through the line 16 and the line 52 by means of a suitable conveying means, for example by means of a pump, and is then diluted at a suitable point in the dialysis- or in the preparation unit so that, optionally after adding a base concentrate, a finished dialysis solution can be provided. This means that the flow path through the connection means and the coupling means as well as through hose of the water used for the dissolving at least regionally corresponds to that via which the liquid concentrate is led off. One and the same pump can also be used to supply the water, on the one hand, and to lead off the liquid concentrate, on the other hand.

As can be seen from FIG. 2, the ports or the lines 51, 52 have stubs onto which the connectors 120, 122 of the receptacle 10 are placed, and e.g. plugged, so that receiving regions of the connectors 120, 122 receive the stubs. For this purpose, recesses or receivers 53, 54 are arranged at the dialysis- or at the preparation unit into which the named stubs project and into which the corresponding connectors 120, 122 are inserted when the container 10 is coupled. In the coupled state, the stubs project into receivers of the connectors 120, 122 or are least connected therewith such that a fluid-tight connection is established. In one embodiment these stubs also provide for the possibility to vent the container 10 by venting means.

The connector 120 is in fluid communication with the hose 16 and the connector 122 is in fluid communication a filter of the container 10. Such a connection can, for example, be achieved by a groove or the like in the wall of the connectors 120, 122, as is described in EP 1 344 550 B1. A chamber which is likewise described in more detail in EP 1 344 550 B1 can be located between the connector 120, 122 and the line 16.

Accordingly, water and air can be supplied to the container 10 and the liquid concentrate can be led off out of the container 10 via the line 52 at the unit side and via the connector 120. Air can be removed or can escape from the container 10 via the line 51 at the unit side and the connector 122.

In the installed state of the receptacle 10, the cover 59 of the dialysis- or of the preparation unit pivotable about the axis 65 is then folded down, i.e. after the coupling of the receptacle 10, so that the stubs 70, 71 arranged at the cover 59 press from above onto the connectors 120, 122 of the connection means 12 and hold them in the coupled position. If no receptacle is used, the stubs 70, 71 can engage into the cut-outs 53, 54 so that a fluid-tight connection likewise results. A purging process can be carried out in this position of the cover.

The reference numeral 60 finally marks the end region of the container 10 which is sealingly connected to the connection element 12.

FIG. 3 shows a first film with the reference film 500 and a second film of an embodiment of the container 10 with the reference numeral 600. A folded region which connects the two films 500 and 600 is marked by the reference numerals 700. This folded region 700 can be designed as a separate part or can be connected in one piece to one of the films 500, 600. As can be seen from FIG. 3, the folded region 700 is formed by two limbs which are arranged acutely to one another, but do not have the same length.

FIG. 3 furthermore shows the opening process of the container 10 from the folded state shown to the left of the arrow and in the unfolded state shown to the right of the arrow.

It is achieved by the limbs of the fold region 700 of unequal lengths that on the unfolding the center of gravity moves less than with limbs of equal length so that the V-shaped tip of the container 10 shown by the reference numeral 710 remains at the bottom, which is of importance for the dissolving process.

The term "film" used within the framework of the present invention is to be interpreted generally and includes any wall material of the container 10. It can be made as elastic, flexible, etc. The films 500, 600 and the fold 700 or the corner region 700 can comprise the same material.

FIG. 4, left hand illustration, shows the container 10 in accordance with FIG. 3 in a longitudinal sectional representation and in a perspective view. The connection means 12 by means of which the container 10 can be coupled to a dialysis- or to a preparation unit for the acid concentrate is arranged in the upper region of the container 10. This connection means is in fluid-tight connection with the adjacent films or wall regions of the container 10.

As can be seen from FIG. 4, a wall of the container 10 is formed by a film and the other wall of the container 10 by the other film which has the fold-like section. It can be seen from the Figures that the container 10 takes up relatively little space in the folded state, but has a large intake volume for the dry concentrate or for the dissolved concentrate in the unfolded state. Provision is made in a preferred embodiment of the invention that the container 10 or its walls is/are manufactured exactly from two films.

FIG. 5 shows the film web which comprises two rows 800, 900 in a plan view. As can be seen from the Figure, the film sections for forming the container walls are formed in trapezoidal shape in a plan view and are arranged in the two webs such that the lower row 900 of the trapezoidal sections is upside down with respect to the upper row 800 of the trapezoidal sections, i.e. is standing on its head. This allows a good utilization of the film material.

As can further be seen from FIG. 5, the clippings 1000 are kept relatively small in this manner and are e.g. likewise not located between the mutually adjacent trapezoids.

As is marked by the reference symbol A, the welding is produced in one step in accordance with the shown pattern M and the cutting of the films takes place in a step B following it likewise in accordance with the pattern M.

FIG. 6 shows the films 500, 600 which form the container 10 in a perspective representation. As can be seen from FIG. 5 and as indicated by arrows, the upper one of the films 500 is first folded in step 1 and then welded to the lower film web 600 in step 2. The step of the cutting of the two films to produce mutually separate containers 10 is not shown in FIG. 5. The reference numeral 1100 marks the apparatus for welding the respective film sections.

In a preferred embodiment of the invention, the individual films are each multilayer films, e.g. two-layer films. One layer represents a sealing layer which has a low melting temperature. The other layer has a higher melting temperature in respect to this and has a mechanical strength or resistance which is good relative thereto.

The use of polyamide (high melting temperature, good resistance properties, transparent and visually appealing) and polyethylene (lower melting temperature, easy to weld) is conceivable. Such a two-layer film represents a good option for manufacturing the container 10 in accordance with the invention. The thickness of the films is e.g. 200 micrometers and the dimensioning of the films is carried out in that the filled container 10 can take up a volume of 5 liters.

FIG. 7 shows the two films 500, 600 which form the later walls of the container 10 in the left hand illustration. In a first method step, the films are rolled off (FIG. 7, left hand illustration). A fold or a kink is then produced in one of the films 500, as can be seen from FIG. 7, middle and right hand representation. This kink is carried out such that the length of the two films in the kinked state of the film 500 is substantially identical. The region formed by two limbs 501 forms a wall of the container 10; the further walls are formed by the adjacent sections of the film 500 and by the film 600.

Furthermore, as a fifth aspect, the invention relates to a method of making an liquid acid concentrate or a dialysis liquid at least comprising step (i):
(i) mixing the concentrate according to the first aspect or one of the embodiments described therein with water, optionally in the presence of a gas such as air.

In one embodiment said mixing is carried out under at least one of the following conditions, e.g. under a combination of conditions 2), 5) and 6):
1) the mixing is carried within the container 10 according to claim 11 or 12;
2) the mixing is carried within the container 10 according to claim 12;
3) the mixing is carried out in the presence of water and air, wherein water is added to the container 10 with a velocity of 600 to 800 ml/min;
4) the mixing is carried out in the presence of water and air, wherein air is added to the container 10 with a velocity of 1 to 3 l/min;
5) the mixing is carried out in the presence of water and air, wherein water is added to the container 10 with a velocity of 600 to 800 ml/min and air is added to the container 10 with a velocity of 1 to 3 l/min;
6) the mixing is carried out at a temperature of from 50° C. to 65° C., e.g. 55° C. to 60° C.

In one embodiment, said making of the dialysis liquid is completed in less than 10 minutes, e.g. in a time frame of 5 to less than 10, e.g. 7 to 9 minutes, in particular in cases where the combination of above conditions 2), 5) and 6) is used. This embodiment is particularly suited to provide a dialysis liquid, such as a liquid acid concentrate in a tailor-made form for one treatment of one patient.

In another embodiment said mixing is carried out within the dialysis or preparation unit at a point in time, where no dialysis takes place.

In a sixth aspect, the present invention furthermore relates to the use of a container 10 in accordance with the present invention for manufacturing an acid liquid concentrate which in turn serves the manufacturing of a dialysis solution, e.g. of a dialysis solution for hemodialysis. In particular under the 5th and 6th aspect, i.e. the provision of the liquid acid concentrate, the beneficial dissolution properties of the dry concentrate play an important role. While during the preparation of a dialysis solution directly from a dry concentrate, significantly larger amounts of water are added to the suitable amount of dry concentrate to provide a physiologically acceptable dialysis solution, within the subject invention, the dry concentrate is dissolved in significantly lower amount of water, i.e. in the range of 1 to 15 liters, e.g. 4 to 6 liters of water, as e.g. outlined hereinbefore in relation to the fourth aspect of the invention.

In a seventh aspect, the invention further relates to the use of an acid liquid concentrate located in a container 10 in accordance with the invention for manufacturing a dialysis solution, e.g. a dialysis solution, which is used for hemodialysis.

The present invention furthermore relates to a dialysis unit or to a preparation unit, with the preparation unit serving the manufacture of a concentrate for a dialysis solution. Provision is made in accordance with the invention that the dialysis- or the preparation unit is coupled to a container 10 in accordance with the invention or is suitable for coupling to such a container 10.

For further details regarding the sixth and seventh aspect references is again made to WO 2010/004263.

According to a further aspect, the invention relates to a dialysis or preparation unit, at least comprising a concentrate for a dialysis liquid according to the first aspect or one of the embodiments described therein or the dialysis liquid resulting from the admixture of water to said concentrate.

In one embodiment said dialysis or preparation unit comprises means for controlling the appropriate mixing of the dry concentrate with the other constituents necessary to provide the desired liquid acid concentrate or the dialysis solution. In one embodiment, said control means are adapted to also control the flow of water and/or a gas during said mixing.

EXAMPLES

The following dry concentrates including the acid component were prepared. The components "minors" and "NaCl/dextr." were respectively obtained by a granulation process following EP 0 287 978. The below numbers (in "g") are to be understood exemplarily and are intended to illustrate on the basis of this example the respective ratios of the constituents present in the dry concentrate.

|  |  |  | 111.50 | 211.50 | 311.50 | 411.50 |
|---|---|---|---|---|---|---|
| granules | minors | $MgCl_2, 6H_2O$ | 18.25 | 18.27 | 18.30 | 18.32 |
|  |  | $CaCl_2, 2H_2O$ | 39.60 | 39.64 | 39.70 | 39.75 |
|  |  | KCl | 13.39 | 26.80 | 40.26 | 53.75 |
|  |  | NaCl | 31.48 | 31.52 | 31.56 | 31.60 |
|  |  | total | 102.73 | 116.24 | 129.81 | 143.41 |
| powder | Citric acid | $C_6H_8O_7$ | 34.50 | 34.54 | 34.58 | 34.63 |
| granules | NaCl/dextr. | NaCl | 1049.45 | 1050.56 | 1051.92 | 1053.28 |
|  |  | dextrose | 179.58 | 179.77 | 180.00 | 180.23 |
|  |  | total | 1229.03 | 1230.33 | 1231.92 | 1233.51 |

The thus obtained granulates were provided in the form of a bag as described with reference to FIG. 1 and admixed with a total amount of water of 4157 g. The resulting liquid concentrate was further dissolved in the dialysis unit in a ratio of 37 to 1. The water was introduced into the bag with a velocity of 700 ml/min together with air in an amount of 2 l/min. After around 7 minutes, complete dissolution was achieved and a dialysis was treatment was conducted. The concentrations (Mmol/ml) within the dialysis solution were as follows:

Citric acid: 1

Cl: 109-111
Ca: 1.5
Mg: 0.5
K: 2 to 4
Na: 103.

The invention claimed is:

1. A dry concentrate suitable to form a liquid acid concentrate or a part of a liquid acid concentrate usable in dialysis comprising
 a first component comprising a first granulate comprising a plurality of first granules comprising sodium chloride and glucose, wherein each of said first granules comprises said sodium chloride and said glucose and
 a second component comprising a second granulate comprising a plurality of second granules, wherein said second granules comprise at least one physiologically acceptable electrolyte, which is different from sodium chloride,
 or a second component in the form of a powder, wherein said powder comprises at least one physiologically acceptable electrolyte which is different from sodium chloride, and wherein said powder comprises a plurality of fine particles, wherein each particle comprises of one of said at least one physiologically acceptable electrolyte, which is different from sodium chloride;
 or a mixture of said second granulate and said powder;
 wherein said dry concentrate is substantially free of a base component that is suitably used in dialysis and wherein the first granulate of the first component or both the first granulate and the second granulate are formed from a granulation process step.

2. The dry concentrate according to claim 1, wherein the first granulate comprises at least 50 wt-% of first granules, based on the total weight of the first granulate in the dry concentrate, which have an equivalent diameter of above 0.5 to below 12.5 mm.

3. The dry concentrate according to claim 1, wherein said second component comprises a cation selected from the cations of magnesium, calcium, potassium, or mixtures of two or more thereof; and comprises an anion selected from chloride, acetate, lactate, or mixtures of two or more thereof.

4. The dry concentrate according to claim 1, further comprising citric acid as a third component.

5. The dry concentrate according to claim 1, wherein said base component is sodium bicarbonate.

6. The dry concentrate according to claim 1, wherein the first granulate comprises at least 90 wt-% of first granules, based on the total weight of the first granulate in the dry concentrate, which have an equivalent diameter of above 0.5 to below 12.5 mm.

7. The dry concentrate according to claim 1, wherein the second component comprises $MgCl_2$, $CaCl_2$ and KCl.

8. The dry concentrate according to claim 1, wherein the first and the second components comprise said first and second granulates.

9. The dry concentrate according to claim 8, wherein the first granules of the first component exhibit a higher average equivalent diameter than the second granules of the second component.

10. The dry concentrate according to claim 8, wherein the second granulate comprises at least 50 wt-% of second granules, based on the total weight of the first granulate in the dry concentrate, which have an equivalent diameter of above 1 to below 5 mm.

11. The dry concentrate according to claim 8, wherein the second granulate comprises at least 90 wt-% of second granules, based on the total weight of the first granulate in the dry concentrate, which have an equivalent diameter of above 1 to below 5 mm.

12. The dry concentrate according to claim 1, wherein the granulates of the first component or the first and the second components are obtainable via a manufacturing process comprising the following:
 dry compressing said NaCl and glucose to obtain first compacts, or dry compressing said NaCl and glucose and the at least one physiologically acceptable electrolyte to obtain first and second compacts, wherein said dry compressing of said first and said dry compressing of said second compacts are conducted separately from each other;
 reducing the size of said first compacts to form the first granulate comprising the plurality of first granules,
 or reducing the size of said first and second compacts to form the first and second granulates comprising a plurality of first and second granules.

13. The dry concentrate according to claim 12,
 wherein the dry compressing comprises passing the NaCl and glucose or the NaCl glucose and the at least one physiologically acceptable electrolyte under pressure between two rolls with parallel axes, which are driven in mutually counter-rotating rotation sense;
 wherein reducing the size of said first and second compacts is achieved by grinding, milling, crushing, or a combination of two or more thereof; and
 wherein said dry compressing and reduction of size are carried out continuously.

14. A container comprising at least the dry concentrate according to claim 1.

15. A dialysis or preparation unit, wherein the preparation unit serves to prepare a liquid concentrate to be used for the preparation of a dialysis solution, comprising at least one concentrate according to claim 1; or a container comprising at least the dry concentrate, wherein the container is connected to the dialysis or preparation unit.

16. A liquid acid concentrate formed from the dry concentrate according to claim 1.

17. A process for the preparation of the dry concentrate according to claim 16 comprising the following:
 dry compressing said NaCl and glucose to obtain first compacts, or dry compressing said NaCl and glucose, and the at least one physiologically acceptable electrolyte to obtain first and second compacts, wherein said dry compressing of said first and said dry compressing of said second compacts are conducted separately from each other;
 reducing the size of said first compacts to form the first granulate comprising the plurality of first granules,
 or reducing the size of said first and second compacts to form the first and second granulates comprising a plurality of first and second granules.

18. The process according to claim 17, wherein said manufacturing process further comprises sieving of said granulates obtained by reducing the size of said compacts through at least two sieves.

19. A method of preparing a liquid acid concentrate which in turn serves the preparation of a dialysis solution, at least comprising (i):
 (i) mixing the concentrate according to claim 1 with water.

20. A method of claim 19, wherein (i) is carried out in the presence of a gas.

* * * * *

UNITED STATES PATENT AND TRADEMARK OFFICE
CERTIFICATE OF CORRECTION

Page 1 of 1

PATENT NO. : 10,918,600 B2
APPLICATION NO. : 16/174311
DATED : February 16, 2021
INVENTOR(S) : Eyrard et al.

It is certified that error appears in the above-identified patent and that said Letters Patent is hereby corrected as shown below:

On the Title Page

Item (72):
"Inventors: Thierry Eyrard, Lyons (FR); Philippe Laffay, Sainte Foy les Lyon (FR); Benoit Luaire, Sourcieux les Mines (FR)" should read --Inventors: Thierry Eyrard, Lyon (FR); Philippe Laffay, Sainte Foy les Lyon (FR); Benoit Luaire, Sourcieux les Mines (FR)--

In the Claims

Claim 13, Column 22, Line 22 "the NaCl glucose" should read --the NaCl, glucose--

Claim 17, Column 22, Line 42 "according to claim 16" should read --according to claim 1--

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*